United States Patent [19]

Orlowski et al.

[11] Patent Number: 5,580,854
[45] Date of Patent: Dec. 3, 1996

[54] SUBSTRATE-RELATED PEPTIDYL-ALDEHYDE INHIBITORS OF THE PROTEOLYTIC ACTIVITY OF THE MULTICATALYTIC PROTEINASE COMPLEX

[75] Inventors: Marian Orlowski; Christopher Cardozo; Alexander Vinitsky, all of New York, N.Y.

[73] Assignee: Mount Sinai School of Medicine of The City University of New York, New York, N.Y.

[21] Appl. No.: 206,789

[22] Filed: Mar. 4, 1994

Related U.S. Application Data

[63] Continuation of Ser. No. 253,185, Jun. 2, 1994, abandoned, which is a continuation of Ser. No. 68,273, May 26, 1993, abandoned, which is a continuation of Ser. No. 801,324, Dec. 2, 1991, abandoned.

[51] Int. Cl.⁶ ..................................................... A61K 38/04
[52] U.S. Cl. ............................................. 514/18; 530/330
[58] Field of Search ............................... 530/330; 514/18

[56] References Cited

PUBLICATIONS

Orlowski, M., Biochemistry 29:10289–10297 (1990).
Ruddinger, J. in "Peptide Hormones", J. A. Parsons, Ed., University Park Press, Baltimore (1976), pp. 1–7, see p. 4 lines 4 ff.
Orlowski, M., J. Lab. & Clin. Med. 121:187–189 (1993).
Tanaka et al., J. Cell. Physiol. 139:34–41 (1989).
Amsterdam et al., Proc. Natl. Acad. Sci. USA 90:99–103 (1993).
Dahlmann et al., FEBS Lett. 251:125–131 (1989).
Eytan et al., Proc. Natl. Acad. Sci. USA 86:7751–7755 (1989).
Rechsteiner et al., J. Biol. Chem. 268:6065–6068 (1993).
Glotzer et al., Nature (London) 349:132–138 (1991).
Ciechanover et al., Proc. Natl. Acad. Sci. USA 88:139–143 (1991).
Murakami et al., Nature (London) 360:597–599 (1992).
Fujiwara et al., J. Biol. Chem. 265:16604–16613 (1990).
Beyon, Intl. Committee on Proteolysis Newsletter, Jan., 1–2 (1994).
Brown et al., Nature (London) 353:355–360 (1991).
Goldberg et al., Nature (London) 357:375–379 (1992).
Wilk and Orlowski, J. Neurochem. 35:1172–1182 (1980).
Wilk and Orlowski, J. Neurochem. 40:842–849 (1983).
Orlowski and Wilk, Biochem. Biophys. Res. Comm. 101:814–822 (1981).
Orlowski et al., Biochemistry 28:9270–9278 (1989).
Orlowski et al., Biochemistry 32:1563–1572 (1993).
Schecter and Berger, Biochem. Biophys. Res. Commun. 27:157–162 (1967).
Cardozo et al., Biochemistry 31:7373–7380 (1992).
Anderson et al., J. Am. Chem. Soc. 86:1839–1842 (1963).
Vinitsky et al., Biochemistry 31:9421–9428 (1992).
Orlowski & Michaud, Biochemistry 28:9270–9277 (1989).
Pfitzner and Moffat, J. Am. Chem. Soc. 87:5661–5670 (1965).
Reingold & Orlowski, J. Neurochem. 32:907–913 (1978).
Goldbarg & Rutenberg, Cancer 11:283–291 (1958).
Bratton & Marshall, J. Biol. Chem. 128:537–550 (1939).
Pfleiderer, Meth. Enzymol. 19:514∞521 (1970).
Almenoff & Orlowski, Biochemistry 22:590–599 (1983).
Dixon, Biochem. J. 55:170–171 (1953).
Orlowski et al., Biochemistry 30:5999–6005 (1991).

*Primary Examiner*—Michael P. Woodward
*Assistant Examiner*—Benet Prickril
*Attorney, Agent, or Firm*—Brumbaugh, Graves, Donohue & Raymond

[57] ABSTRACT

The present invention provides novel peptidylaldehyde inhibitors of proteolysis mediated by the multicatalytic proteinase complex (MPC) or proteasome. The inhibitors have the general formula $$Z\text{-}P_4\text{-}P_3\text{-}P_2\text{-}P_1\text{-}CHO \quad (I)$$

wherein $P_1$ is selected from among branched chain amino acids occurring naturally in proteins and norleucine;

$P_2$ is selected from among non-polar L-amino acids;

$P_3$ is proline or hydroxyproline;

$P_4$ is selected from among non-polar L-amino acids;

CHO is an aldehyde replacement for the COOH group on the $P_1$ amino acid; and

Z is an amino blocking group attached to the $NH_2$ group on the $P_4$ amino acid.

The amino blocking group Z may be chosen from among benzyloxycarbonyl, benzoylglycine, tertiary butoxycarbonyl, acetylbenzyloxycarbonyl, benzoylglycine, tertiary butoxycarbonyl, acetyl or other $NH_2$ blocking groups known in protein and peptide chemistry. The inhibitors inhibit intracellular protein degradation in cells, as well as inhibit mitosis and proliferation of dividing cell populations. As such, the inhibitors have use in inhibiting undesired intracellular proteolysis and mitosis in excessively proliferating cells.

24 Claims, 3 Drawing Sheets

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1..4

( x i ) SEQUENCE DESCRIPTION: SEQ ID NO:1:

Gly  Pro  Phe  Leu
1

( 2 ) INFORMATION FOR SEQ ID NO:2:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1..4

( x i ) SEQUENCE DESCRIPTION: SEQ ID NO:2:

Gly  Pro  Ala  Leu
1

( 2 ) INFORMATION FOR SEQ ID NO:3:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide ( i x ) FEATURE:
( A ) NAME/KEY: Peptide
( B ) LOCATION: 1..4

( x i ) SEQUENCE DESCRIPTION: SEQ ID NO:3:

Gly  Pro  Phe  Val
1

( 2 ) INFORMATION FOR SEQ ID NO:4:

( i ) SEQUENCE CHARACTERISTICS:
( A ) LENGTH: 4 amino acids
( B ) TYPE: amino acid
( D ) TOPOLOGY: linear ( i i ) MOLECULE TYPE: peptide (ix) FEATURE:
    (A) NAME/KEY: Peptide
    (B) LOCATION: 1..4

(xi) SEQUENCE DESCRIPTION: SEQ ID NO:4:

Pro Gly Ala Leu
1

(2) INFORMATION FOR SEQ ID NO:5:

(i) SEQUENCE CHARACTERISTICS:
        (A) LENGTH: 4 amino acids
        (B) TYPE: amino acid
        (D) TOPOLOGY: linear     (ii) MOLECULE TYPE: peptide     (ix) FEATURE:
        (A) NAME/KEY: Peptide
        (B) LOCATION: 1..4

(xi) SEQUENCE DESCRIPTION: SEQ ID NO:5:

Gly Pro Ala Phe
1

SUBSTRATE-RELATED PEPTIDYL-ALDEHYDE INHIBITORS OF THE PROTEOLYTIC ACTIVITY OF THE MULTICATALYTIC PROTEINASE COMPLEX

The invention disclosed herein was made during the course of a grant funded by the United States government and is thus subject to the rights of the government therein.

This application is a continuation of Ser. No. 253,185 filed Jun. 2, 1994 now abandoned, which is a continuation of Ser. No. 68,273 filed May 26, 1993 now abandoned, which is a continuation of Ser. No. 801,324 filed Dec. 2, 1991 now abandoned.

TECHNICAL FIELD

The present invention relates to protein and peptide chemistry. More particularly, it relates to the discovery and isolation of novel inhibitors of proteolysis in cells mediated by the multicatalytic proteinase complex ("MPC") or proteasome. The inhibitors, which are synthetic peptide derivatives, correspond in amino acid sequence to natural and synthetic substrates recognized and cleaved by the MPC. Moreover, the inhibitors inhibit the proteolytic activity of the MPC, as well as certain biological functions mediated by the MPC, e.g., intracellular protein degradation and mitosis.

Thus, these inhibitors are useful in inhibiting intracellular proteolysis, and can find special use eukaryotic recombinant DNA expression systems, where proteolysis of protein products resulting from recombinant DNA expression may be a problem in obtaining significant yields of protein product. The inhibitors of the invention may also be used to inhibit mitotic activity in proliferating cells, in which proteolysis, believed to be mediated by the MPC, plays a significant role.

Furthermore, the inhibitors of the invention may also be used to interfere with intracellular functions of the MPC and, therefore, are useful for inhibiting excessive intracellular protein degradation, such as in cachexians inhibiting mitotic activity in excessively proliferating cells and inhibiting unwanted immunological responses, such as autoimmune diseases and transplant rejections.

BACKGROUND OF THE INVENTION

The multicatalytic proteinase complex (MPC), also referred to as the proteasome, is an unusually high molecular weight proteinase (about 700 kDa, 19S), that is found in both the cytoplasm and nucleus of a wide variety of eukaryotic cell types. The MPC is composed of about 28 low molecular weight subunits (21,000–34,000 daltons) of which 13–15 are non-identical. See, e.g., Orlowski, M., Biochemistry 29:10289–10297 (1990) and Orlowski, M., J. Lab. & Clin. Med. 121:187–189 (1993) for reviews.

The subunits of the MPC are organized in four stacked rings, each composed of 6–7 subunits surrounding a central water-filled canal. The MPC is highly conserved evolutionarily, having been found in all eukaryotic cells studied, and may constitute up to 0.5–1.0% of the total protein in tissue homogenates. The MPC has been found in both the cytoplasm and nucleus of cells, suggesting a functional role in both of these compartments. (Tanaka et al., J. Cell Physiol. 139:34–41 (1989); Amsterdam et al., Proc. Natl. Acad. Sci., USA 90:99–103 (1993)). A variety of evidence suggests that the MPC is essential for cell viability and proliferation, that it is involved in antigen processing, degradation of nuclear oncoproteins and control of the mitotic cycle through degradation of cyclins.

Adding to its importance in regulating a variety of biological effects is the finding that the MPC is conserved across the evolutionary spectrum, as indicated by immunological cross-reactivity of complexes from eukaryotic species as diverse as yeast, Drosophila and mammalian species. Moreover, a related, but simpler, protein composed of only two subunits has been found in archaebacteria (see Dahlmann et al., FEBS Lett. 251:125–131 (1989)).

The MPC is believed to constitute the catalytic core of a large 26S multisubunit cytoplasmic particle, apparently required inter alia for the ubiquitin-dependent and ubiquitin-independent pathways of intracellular proteolysis (Eytan et al., Proc. Natl. Acad. Sci. USA 86:7751–7755 (1989); Rechsteiner et al., J. Biol. Chem. 268:6065–6068 (1993)). These pathways are believed to be involved in the degradation of cyclins and other short-lived proteins such as nuclear oncogene products (Glotzer et al., Nature (London) 349:132–138 (1991)); Ciechanover et al., Proc. Natl. Acad. Sci. USA 88:139–143 (1991)) and ornithine decarboxylase (Murakami et al., Nature (London) 360:597–599 (1992)). These findings suggest a role of the MPC in regulating cell growth and division (mitosis). Additional studies demonstrated a change in the distribution and activity of the MPC with stages in the cell cycle and that disruption in any one of 12 out of 13 genes encoding yeast MPC subunits results in an arrest in cellular proliferation or an inability to degrade proteins, also suggesting a role for the MPC in cellular growth and division (Fujiwara et al., J. Biol Chem. 265:16604–16613 (1990); Beynon, Int. Committee on Proteolysis News Letter, January, 1–2 (1994)).

The MPC also appears to be required for proper antigen processing by cells of the immune system, based on observations that low molecular weight peptides ("LMPs"), which are structurally similar (homologous) to MPC subunits, are precipitated by antibodies to class I major histocompatibility (MHC) molecules (Brown et al., Nature (London) 353:355–360 (1991)). Moreover, genes for LMPs have been mapped to the class II region of the MHC (Goldberg et al., Nature (London) 357:375–379 (1992)). In addition, MPC and LMP have similar subunit patterns and, as noted, serologically cross-react. All of these observations indicate that the MPC may be responsible for processing and presentation of MHC class I antigens, which are involved in numerous immunological functions and reactions.

While much is known about the biochemistry and functions of the MPC, there is still much that remains unanswered. For example, questions such as how many of the subunits are proteolytically active and what activities are expressed by different subunits have not been answered. Dissociation of the complex results in total loss of proteolytic activity, and all attempts to isolate active subunits have resulted in failure. The integrity of the intact proteasome appears to be required for biological activity. Thus, studies on the specificity of the various MPC components require using the intact, native complex.

Early studies of the MPC led to the delineation of three different proteolytic activities, each associated with a distinct component of the complex (Wilk and Orlowski, J. Neurochem. 35:1172–1182 (1980); Wilk and Orlowski, J. Neurochem. 40:842–849 (1983); Orlowski and Wilk, Biochem. Biophys. Res. Comm. 101:814–822 (1981)). These three activities have been classified, on the basis of the amino acid residues in the $P_1$ position of the cleaved substrate, as (1) trypsin-like (T-L; cleavage on the carboxyl side of basic residues), (2) chymotrypsin-like (ChT-L; cleavage on the carboxyl side of hydrophobic residues) and (3) peptidylglutamyl-peptide hydrolyzing (PGPH; cleavage on the carboxyl side of glutamyl residues). All three components possess activity toward peptidyl-arylamide bonds. Each of these three activities is inactivated by 3,4-dichloroisocoumarin (DCI), which is known to react with serine residues in the active site of proteases (Orlowski et al., Biochemistry 28:9270–9278 (1989)).

Recent studies have elucidated two additional proteolytic components of the MPC, one which cleaves preferentially on the carboxyl side of branched chain amino acids, designated (BrAAP), and the other, designated SNAAP, which cleaves on the carboxyl side of the small neutral amino acids, alanine and glycine (designated SNAAP) (Orlowski et al., Biochemistry 32:1563–1572 (1993)). Neither the BrAAP nor SNAAP components are capable of cleaving peptidyl-arylamide bonds. Moreover, the BrAAP component is greatly activated upon exposure of the MPC to DCI.

A significant body of evidence indicates that the BrAAP component represents a major factor in protein degradation and that this component may be responsible for most of the protein-degrading activity of the MPC. Thus, the identification and elucidation of the BrAAP component substrate specificity and design of synthetic inhibitors of the MPC (BrAAP component) has use in inhibiting intracellular protein degradation, MHC-mediated immunological reactivities, as well as effecting inhibition of intracellular proteolysis and inhibition of cellular growth and division.

DISCLOSURE OF THE INVENTION

In accordance with the present invention, a number of inhibitors of the MPC have been synthesized. These inhibitors are peptide analogs that inhibit the proteolytic activity of the BrAAP component of the MPC towards natural protein substrates, as well as synthetic substrates. As noted, the BrAAP component of the MPC cleaves preferentially peptide bonds on the carboxyl side of branched chain amino acids, e.g., leucine (Leu), isoleucine (Ile) and valine (Val).

Moreover, the inhibitors of the present invention inhibit intracellular protein degradation, primarily of short-lived proteins, as well as inhibit mitosis and cellular proliferation in eukaryotic cells.

The novel inhibitors of the present invention comprise aldehyde derivatives of tetrapeptides. The inhibitors all contain an amino blocking group attached to the $NH_2$ group of the amino terminal amino acid of the inhibitor and have an aldehyde, rather than a carboxyl group, at their carboxyl terminus. The amino blocking group may be benzyloxycarbonyl (Cbz), benzoylglycine (hippurate), tertiary butoxycarbonyl (tBOC), acetyl (Ac) or other $NH_2$ blocking agents known in protein and peptide chemistry. Cbz is the preferred blocking group.

Preferably, the inhibitors contain a branched chain amino acid, most preferably leucine (Leu), in the $P_1$ (C-terminal) position and a proline (Pro) in the $P_3$ position. The standard three letter codes for amino acids are used throughout this disclosure. The nomenclature of Schecter and Berger, Biochem. Biophys. Res. Commun. 27:157–162 (1967), incorporated herein by reference, is used to designate the position ("P") of the amino acid in the inhibitors disclosed herein and the corresponding subsites ("S") in the active site of the target enzyme. Specifically, such inhibitors are designed to inhibit the BrAAP component of the MPC. The inhibitors are apparently ineffective against the T-L activity and are less inhibitory toward the ChT-L and PGPH activities.

In a general aspect, the present invention provides novel inhibitors of the proteolytic activity of the MPC having the general formula $$Z-P_4-P_3-P_2-P_1-CHO \qquad (I)$$

wherein $P_1$ is selected from among branched chain amino acids;

$P_2$ is selected from among non-polar L-amino acids;

$P_3$ is proline or an analog thereof;

$P_4$ is selected from among non-polar L-amino acids;

CHO is an aldehyde replacement for the COOH group on the $P_1$ amino acid; and

Z is an amino blocking group attached to the $NH_2$ group on the $P_4$ amino acid.

The branched chain amino acids herein include the naturally occurring leucine, valine and isoleucine, as well as non-naturally occurring branched chain amino acids, e.g. norleucine. By naturally occurring is meant amino acids found in proteins and polypeptides. Preferably, $P_1$ is leucine, $P_2$ is phenylalanine or alanine, $P_3$ is proline or an analog thereof, e.g., hydroxyproline, and $P_4$ is glycine, proline or leucine. The amino blocking group Z may be benzyloxycarbonyl (Cbz), benzoylglycine (hippurate), tertiary butoxycarbonyl (tBOC), acetyl (Ac) or other groups known in protein and peptide chemistry to be useful as $NH_2$ group blocking agents. Z is preferably benzyloxycarbonyl (Cbz).

In a preferred embodiment, the inhibitor has the sequence Cbz-Gly-Pro-Phe-Leu-CHO (the amino acid sequence of which is designated as SEQ ID NO. 1). Other preferred embodiments include Cbz-Gly-Pro-Ala-Leu-CHO (the amino acid sequence of which is designated as SEQ ID NO. 2) and Cbz-Gly-Pro-Phe-Val-CHO (the amino acid sequence of which is designated as SEQ ID NO. 3).

A further aspect of the present invention is that it provides inhibitors of intracellular protein degradation. Also provided are methods of inhibiting intracellular protein degradation in which the inhibitors of the present invention are provided to cells in an amount sufficient to inhibit intracellular protein degradation.

The ability of the inhibitors of the present invention to inhibit intracellular protein degradation indicates their usefulness in situations where such inhibition may be required, such as in recombinant DNA expression by eukaryotic expression systems for the production of useful heterologous proteins. Thus, a further aspect of the present invention is the use of the inhibitors of the present invention to inhibit heterologous protein degradation in eukaryotic expression systems, including yeast and mammalian cells, for the recombinant production of heterologous proteins. By heterologous here is meant proteins that are not normally produced by the host cells of the expression system.

A still further aspect of the present invention is the use of the inhibitors of the invention as inhibitors of mitosis and cell proliferation. Also provided are methods for inhibiting mitosis using the inhibitors of the present invention.

Further, the inhibitors of the invention may also be used to interfere with intracellular functions of the MPC, and, therefore, are useful for inhibiting excessive intracellular protein degradation, such as in cachexias, inhibiting mitotic activity in excessively proliferating cells, and inhibiting unwanted immune responses, such as autoimmune disease and transplant rejections.

DESCRIPTION OF THE INVENTION

The present invention is directed to novel compounds that inhibit the proteolytic activity of the multicatalytic proteinase complex (MPC) or proteasome. Such inhibitors not only directly inhibit the proteolytic activity of the MPC, but also inhibit other biologic functions which involve the MPC, such as intracellular protein degradation and cell proliferation and mitosis. Thus, the inhibitors of the present invention are also intracellular proteolysis inhibitors, as well as mitotic inhibitors.

More particularly, the compounds inhibit the activity of the MPC which cleaves protein substrates on the carboxyl side of branched chain amino acids (hereinafter "BrAAP"). Even more particularly, the BrAAP inhibitors of the present invention are peptidyl aldehydes. Even more particularly, the inhibitors are tetrapeptide aldehydes, in which an aldehyde group has replaced the carboxyl group at the carboxyl terminus of the peptide (i.e., position $P_1$). In addition, the peptidyl aldehydes also contain an amino blocking group attached to the $NH_2$ group of the amino terminal amino acid ($P_4$) The amino blocking group may be benzyloxycarbonyl (Cbz), benzoylglycine (hippurate), tertiary butoxycarbonyl (tBOC) or acetyl (Ac) or other $NH_2$ blocking agents known to be useful in protein and peptide chemistry.

In general, the novel inhibitors of the present invention have the formula $$Z\text{-}P_4\text{-}P_3\text{-}P_2\text{-}P_1\text{-}CHO \qquad (I)$$

where $P_1$ is selected from among branched chain amino acids;

$P_2$ is selected from among non-polar L-amino acids;

$P_3$ is proline or an analog thereof;

$P_4$ is selected from among non-polar L-amino acids;

CHO is an aldehyde replacement for the COOH group on the $P_1$ amino acid; and

Z is an amino blocking group attached to the $NH_2$ group on the $P_4$ amino acid.

Thus, the presence of an aldehyde analog of a branched chain amino acid in the $P_1$ position, of a proline or proline analog in the $P_3$ position, and a non-polar L-amino acid in the $P_2$ and $P_4$ positions is necessary for interaction of the aldehyde group of the inhibitor with the catalytic site of the BrAAP component. As noted above, the amino blocking group Z may be benzyloxycarbonyl (Cbz), benzoylglycine (hippurate), tertiary butoxycarbonyl (tBOC), acetyl (Ac) or other groups known in protein and peptide chemistry to be useful as $NH_2$ group blocking agents. Z is preferably benzyloxycarbonyl (Cbz).

The $P_1$ branched chain amino acids herein include the naturally occurring leucine, valine and isoleucine, as well as non-naturally occurring branched chain amino acids, e.g., norleucine. By naturally occurring is meant amino acids normally occurring in proteins and polypeptides. The $P_3$ amino acid may be proline or a proline analog, e.g., hydroxyproline or related synthetic analog.

The most potent of the BrAAP inhibitors have a prolyl residue in the $P_3$ position and a leucinal (i.e., leucine aldehyde) residue in the $P_1$ position. The inhibitors appear to require a non-polar L-amino acid in both the $P_2$ and $P_4$ positions. Inhibitors having a phenylalanine or an alanine in the $P_2$ position are particularly preferred, although other non-polar L-amino acids may be substituted therefor. Such non-polar amino acids may be naturally occurring, as defined above, or non-naturally occurring. Inhibitors having a glycine, proline or leucine in the $P_4$ position are also preferred, although other non-polar L-amino acids may be substituted therefor. Likewise, such non-polar amino acids may be naturally occurring or non-naturally occurring. Inhibitors where Z is benzyloxycarbonyl (Cbz) are also preferred, although other amino blocking agents, such as tBOC and Ac may be substituted therefor.

In accordance with the present invention, those skilled in the art would be able to readily make and use the inhibitors of the BrAAP component of the MPC, based upon the parameters for the inhibitors provided herein as well as on an analysis of the amino acid sequence of synthetic substrates for the enzyme, also disclosed herein.

A preferred inhibitor of the present invention is the tetrapeptide aldehyde

Cbz-Gly-Pro-Phe-Leu-CHO.

The amino acid sequence of the above inhibitor is set forth as SEQ ID No. 1.

Additional preferred inhibitors include

Cbz-Gly-Pro-Ala-Leu-CHO and

Cbz-Gly-Pro-Phe-Val-CHO.

The amino acid sequences of the above two inhibitors are set forth as SEQ ID Nos. 2 and 3, respectively.

Additional inhibitors in accordance with the present invention may be readily made and used by those skilled in the art, given the present disclosure and the specific parameters of the novel inhibitors.

The BrAAP component of the MPC has been shown to cleave peptide bonds in proteins on the carboxyl side of branched chain amino acids, e.g., leucine, isoleucine and valine, based upon cleavage studies using natural substrates, such as neurotensin and proinsulin. Such studies, plus those using synthetic peptide substrates, including those disclosed herein, indicate that a proline or glycine residue in the $P_3$ position of the target protein or synthetic peptide substrate is important for directing the substrate to the active site of the BrAAP component, provided that a branched chain amino acid residue, particularly leucine, is present in the $P_1$ position. As noted previously, the nomenclature of Schecter and Berger, Biochem. Biophys. Res. Commun. 27:157–162 (1967), incorporated herein by reference, is used to designate the position ("P") of the amino acid residues in the substrates and inhibitors disclosed herein and the corresponding subsites ("S") in the active site of the enzyme, i.e., the BrAAP component.

The BrAAP component has been shown to be responsible for cleavage of the Ile¹²-Leu¹³ bond in neurotensin (pGlu-Leu-Tyr-Glu-Asn-Lys-Pro-Arg-Arg-Pro-Tyr-Ile↓-Leu; the arrow indicates the site of cleavage) and for cleavage of the Leu⁴⁴-Ala⁴⁵ and Val³⁹-Gly⁴⁰ bonds in the connecting peptide (C-peptide) of bovine proinsulin (Cardozo et al., Biochemistry 31:7373–7380 (1992)).

Moreover, in another study, Orlowski et al., Biochemistry 32:1563–1522 (1993), incorporated herein by reference, the BrAAP component was shown to cleave the Leu-Gly and Leu-Ala bonds in the prototype synthetic substrates Cbz- Gly-Pro-Ala-Leu-Gly-p-aminobenzoate ("pAB") and Cbz-Gly-Pro-Ala-Leu-Ala-pAB, respectively. The activity of the BrAAP component, measured by cleavage of these substrates, was activated by 3,4-dichloroisocoumarin (DCI), a serine protease inhibitor, that inactivates the ChT-L, T-L and PGPH- components of the MPC. BrAAP was also shown to be activated by N-ethylmaleimide, $Mg^{2+}$, $Ca^{2+}$ and low concentrations of sodium dodecyl sulfate (SDS) and fatty acids.

The present invention also discloses additional synthetic substrates for the BrAAP component that are homologous to the aforementioned prototype substrates and show significant substrate activity. These additional substrates have been used to further select and define inhibitor sequences that are effective in inhibiting the BrAAP component.

The practice of the present invention employs, unless otherwise indicated, conventional techniques of synthetic organic chemistry, protein chemistry, molecular biology, microbiology, and recombinant DNA technology, which are well within the skill of those in the art. Such techniques are explained fully in the literature. See, e.g., Scopes, R. K., *Protein Purification Principles and Practices*, 2d ed. (Springer-Verlag, 1987), *Methods in Enzymology* (S. Colowick and No. Kaplan, eds., Academic Press, Inc.), Sambrook et al., *Molecular Cloning: A Laboratory Manual*, 2d ed., Cold Spring Harbor Press, Cold Spring Harbor, N.Y., 1989, *Handbook of Experimental Immunology*, Vols. I–IV (D. M. Weir and C. C. Blackwell, eds., 1986, Blackwell Scientific Publications); House, *Modern Synthetic Reactions*, 2d ed., Benjamin/Cummings, Menlo Park, Calif., 1972.

The inhibitors of the invention may be synthesized by peptide chain elongation of commercially available (Sigma Chemical Coo, St. Louis, Mo.) Cbz-dipeptides or other amino-blocked blocked dipeptides, e.g., tBOC-dipeptides, using the N-hydroxysuccinimide active ester method of Anderson et al., J. Am. Chem. Soc. 86:1839–1842 (1963) to produce tetrapeptidyl alcohols. Oxidation of the peptidyl alcohols using the dimethylsulfoxide-carbodiimide reaction technique, as modified by the inventors (Wilk & Orlowski, J. Neurochem. 35:1172–1182; Vinitsky et al., Biochemistry 31:9421–9428 (1992)) resulted in the formation of the tetrapeptidyl aldehyde inhibitors of the invention.

Following synthesis, the inhibitors are purified by silica gel chromatography, with material absorbing at 260 nm checked for a positive dinitrophenylhydrazone test. Inhibitors elute in a single peak after reversed phase high pressure liquid chromatography. The amino acid compositions of the inhibitors may be determined by standard amino acid analysis techniques following digestion of the inhibitors in 6N HCl. Alternatively, the inhibitors may be characterized using NMR spectroscopy or thin-layer chromatography (TLC).

The inhibitors of the present invention inhibit the proteolytic activity of the BrAAP component of the MPC as determined by their ability to inhibit the degradation of protein substrates, e.g., β-casein and histone $H_3$.

Moreover, the inhibitors have been shown to inhibit mitosis and cellular proliferation in vitro as determined using cultured rat aortic smooth muscle cells and the A549 human lung carcinoma cell line. The inhibitors of the invention inhibit the incorporation of $^3$H-thymidine into the DNA of proliferating cell cultures, indicating an arrest of proliferation. In addition, the inhibitors of the invention have been shown to inhibit proliferation of cells by reducing the numbers of cells in inhibitor-treated cultures versus untreated cultures.

The inhibitors also have been shown to inhibit intracellular protein degradation. Addition of the inhibitors to the A549 cell line results in the inhibition of intracellular proteolysis measured by a decrease in $^{35}$S-methionine in trichloracetic acid soluble material from inhibitor treated versus untreated cells.

In view of the above noted properties of the inhibitors of the present invention, it is contemplated that the present inhibitors may be used in inhibiting mitosis upon administration to dividing cell populations. Another aspect of the invention is thus directed to methods of inhibiting cell proliferation by administering the inhibitors of the present invention to dividing cells for a time and in an amount sufficient to inhibit mitosis.

In addition, it is also contemplated that the inhibitors of the present invention may also be used in inhibiting intracellular protein degradation upon administration to cells. A specific use for such an activity may be found in biotechnology. In this regard the inhibitors of the invention are contemplated for use in inhibiting proteolysis in eukaryotic expression systems producing heterologous proteins via recombinant DNA technology. Such systems would include yeast as well as mammalian host systems. The inhibitors may be used to decrease degradation of proteins, which often reduces the yield of proteins produced in such eukaryotic expression systems.

A further aspect of the invention is directed to methods of inhibiting intracellular protein degradation by administering the inhibitors of the invention to cells for a time and in an amount to reduce intracellular proteolysis.

It is also contemplated that the inhibitors of the invention may also be used to interfere with intracellular functions of the MPC, and, therefore, are useful for inhibiting excessive intracellular protein degradation, such as in cachexias, inhibiting mitotic activity in excessively proliferating cells, and inhibiting unwanted immune responses, such as autoimmune disease and transplant rejections.

The following examples further illustrate the invention.

EXAMPLE 1

The MPC was isolated from frozen bovine pituitaries, obtained from PelFreeze, Inc. (Rogers, Ark.) essentially as described in Orlowski & Michaud, Biochemistry 28:9270–9277 (1989), incorporated herein by reference.

Essentially the MPC was isolated as follows:

Bovine pituitaries (98 g) were washed free of blood and homogenized in 5 volumes of 0.01M Tris-HCl buffer, pH 7.5. After centrifugation for 15 min at 27000 g, the precipitate was washed with 300 ml of the same buffer, centrifuged as above and the combined supernatants were treated with solid ammonium sulfate (24.3 g/100 ml). The precipitate was discarded after centrifugation and the supernatant was treated with additional ammonium sulfate (13.2 g/100 ml). The pellet was dissolved in 15 ml of a Tris-EDTA buffer (0.01 M, pH 7.34) and dialyzed against 7 l of the same buffer. The enzyme was then applied to the top of a DEAE-Sephacel column (50 ml), equilibrated with the same buffer. After washing the column with the same buffer, elution was carried out with a linear gradient established between 200 ml of the same buffer and 200 ml of a 0.3M Tris-EDTA of the same pH. Fractions containing activity were applied to an Ultrogel ACA22 column (5×50 cm) equilibrated with 0.01M Tris-EDTA buffer (pH 8.3). The column was eluted with the same buffer and fractions containing activity were applied to a DEAE-Sephacel column equilibrated with the same buffer. The enzyme was eluted with a linear gradient established between 150 ml of the same buffer and 150 ml of a 0.4M Tris-EDTA buffer pH 8.3. Fractions containing activity were concentrated to about 20 ml and applied in the same day to the top of an Ultragel ACA22 column (5×50 cm) equilibrated with a 0.01 m Tris-EDTA buffer (pH 7.5) and eluted with the same buffer. The enzyme emerged as a single peak of activity after about 540 ml of the buffer passed through the column.

Aliquots of the enzyme (0.5ml) containing 0.5mg protein/ ml were stored frozen at −20° C. and thawed prior to use.

EXAMPLE 2

The inhibitors Cbz-Gly-Pro-Phe-Leu-CHO, Cbz-Gly-Pro-Ala-Leu-CHO and Cbz-Gly-Pro-Phe-Val-CHO were synthesized by oxidation from corresponding peptidyl alcohols. Control peptidyl aldehyde compounds, Cbz-Pro-Gly-Ala-Leu-CHO (SEQ ID No. 4) and Cbz-Gly-Pro-Ala-Phe-CHO (SEQ ID No. 5) that only weakly inhibit the activity of the BrAAP component of the MPC were also synthesized from the corresponding peptidyl alcohols by oxidation.

Peptidyl alcohols were synthesized by peptide chain elongation using the N-hydroxysuccinimide active ester method (Anderson et al., J. Am. Chem. Soc. 86:1839–1842 (1963)). Thus, Cbz-Gly-Pro or Cbz Pro-Gly (each obtained from Sigma Chemical Co., St. Louis, Mo.) were reacted in tetrahydrofuran with N-hydroxysuccinimide and dicyclohexylcarbodiimide to yield the active ester. A solution of the ester in tetrahydrofuran was then added dropwise to an aqueous solution containing a 10% molar excess of either alanine or phenylalanine and sodium carbonate. The pH was maintained at about 9.0 and the progress of the reaction was monitored by subjecting aliquots of the reaction mixture to high pressure liquid chromatography as described in Example 3.

After completion of the reaction, the solvent was removed by evaporation under reduced pressure, and the residue was dissolved in water and acidified to pH 2 with 6 N HCl. The precipitated material was extracted into ethyl acetate, and the ethyl acetate solution was dried with anhydrous sodium sulfate. The solvent was removed by evaporation and the isolated peptide was purified by crystallization from a mixture of either ethanol- or methanol-water.

The isolated peptide was then converted to the active N-hydroxysuccinimide ester as described above and reacted in tetrahydrofuran with either L-leucinol, L-valinol or L-phenylalaninol, the alcohol derivatives of leucine, valine and phenylalanine, respectively, obtained from Sigma Chemical Corp., St. Louis, Mo.). After removal of the solvent, the peptidyl alcohol was dissolved in chloroform, and the chloroform solution was washed twice with sodium carbonate (0.5M), hydrochloric acid and water, and dried by addition of anhydrous sodium sulfate. Removal of the sodium sulfate by filtration and evaporation of the solvent yielded the peptidyl alcohol. The progress of all reactions was followed by subjecting aliquots of the reaction mixtures to HPLC on a reverse phase $C_{18}$ column as described in Example 3.

EXAMPLE 3

Oxidation of the peptidyl alcohols synthesized as provided in Example 2 resulted in the production of the Cbz-blocked tetrapeptide aldehydes, whose amino acid sequences are set forth as SEQ ID Nos. 1–5.

Oxidation of the peptidyl alcohol to the corresponding aldehydes was carried out by a modification (Wilk & Orlowski, J. Neurochem. 35:1172–1182 (1983); Vinitsky et al., Biochemistry 31:9421–9428 (1992)) of the dimethylsulfoxide-carbodiimide reaction described by Pfitzner and Moffat, J. Am. Chem. Soc. 87:5661–5670 (1965). Formation of the aldehydes was followed by reacting aliquots of the reaction mixture with 2,4-dinitrophenylhydrazine to form the corresponding dinitrophenylhydrazones as described previously (Reingold & Orlowski, J. Neurochem. 32:907–913 (1978)). The peptidyl aldehydes were extracted into chloroform and the chloroform solution was washed twice in a separatory funnel with water. After drying the chloroform layer with anhydrous sodium sulfate, the peptidyl-aldehydes were further purified by flash chromatography on a silica gel column by applying the chloroform solution to the top of a silica gel column, and elutioning the peptidyl aldehyde with a mixture of methanol-chloroform (5:95). Fractions of about 20 ml were collected and monitored for the presence of material giving absorbance at 260 nm and a positive dinitrophenylhydrazone test. The tubes containing the aldehyde product were pooled and the peptidyl aldehydes were isolated after removal of the solvent.

All peptidyl aldehydes gave single peaks by HPLC by chromatography on a $c_{18}$ reverse phase uBondapak column (3.9×300 mm; Waters) with elution of the bound peptidyl aldehydes using a linear gradient of 10% to 60% acetonitrile in 0.1% trifluoroacetic acid for 20 minutes, with the 60% acetonitrile-trifluoracetic acid mixture maintained for another five minutes. Some of the physical properties of the peptidyl-aldehydes synthesized above are set forth in Table I.

TABLE I

| Peptidyle Aldehyde | HPLC retention time | Rf TLC: 5% MeOH—CHCl$_3$ |
| --- | --- | --- |
| 1. Cbz-Gly-Pro-Ala-Leu-CHO | 20.2 | 0.41 |
| 2. Cbz-Gly-Pro-Phe-Leu-CHO | 23.9 | 0.59 |
| 3. Cbz-Gly-Pro-Phe-Val-CHO | 23.2 | 0.41 |
| 4. Cbz-Pro-Gly-Ala-Leu-CHO | 20.0 | 0.27 |
| 5. Cbz-Gly-Pro-Ala-Phe-CHO | 20.2 | 0.25 |

The NMR (in CDCl$_3$) values obtained for each of the five peptidyl aldehydes were as follows:
1. Cbz-Gly-Pro-Ala-Leu-CHO:

δ0.8–1 [6H, 2t, CH(C$\underline{H}_3$)2], 1.3–1.5 [3H,m,CH-C$\underline{H}_3$], 1.5–3.3 [7H,m,CHC$\underline{H}_2$CH(CH$_3$)$_2$, C$\underline{H}_2$C$\underline{H}_2$CHNCHCO], 3.4–3.6 [2H,d,NHC$\underline{H}_2$CO],3.6–4.1 [3H,m,3×NHC$\underline{H}$CO], 4.2–4.5 [2H, m, NC$\underline{H}_2$CH$_2$CH$_2$CHCO], 5–5.2 [2H,m, C$_6$H$_5$C$\underline{H}_2$], 5.5–5.7 [1H, m, N$\underline{H}$], 6.9–7.1 [2H,2d, 2×N$\underline{H}$], 7.2–7.4 [5H, s, C$_{6H5}$], 9.4–9.6 [1H, d, C$\underline{H}$O].
2. Cbz-Gly-Pro-Ph$\overline{e}$-Leu-CHO:

δ0.8–1 [6H, 2t, CH(C$\underline{H}_3$)$_2$], 1.5–2.3 [7H, m, CHC$\underline{H}_2$C H(CH$_3$)$_2$, C$\underline{H}_2$C$\underline{H}_2$CHNCHCO], 3.2–3.5 [3H, m, C$_6$H$_5$C $\underline{H}$HNCH$_2$CH$_2$CH$_2$CHCO], 3.8 [2H, d, NHC$\underline{H}_2$CO], 4.3–4.5 [2H, m, 2×NHC$\underline{H}$CO], 4.6–4.8 [1H, m, C$_6$H$_5$C$\underline{H}$], 5–5.2 [2H, m, C$_6$H$_5$C$\underline{H}_2$OCO], 5.4–5.6 [1H, m, NH], 6.7–7 [2H, m, 2×NHC$\underline{H}$CO]. 7.1–7.3 [5, m, C$_6$$\underline{H}_5$CH$_2$], 7.3–7.4 [5, m, C$_{6H5}$CH$_2$OCO], 9.5 [1, s, C$\underline{H}$O ].
3. Cbz-Gly-Pro-Phe-Val-CHO:

δ0.8–1 [6H, 2t, CH(C$\underline{H}_3$)2], 1.5–2.3 [5H, m, CHC $\underline{H}$(CH$_3$)$_2$], NCH$_2$C$\underline{H}_2$CHCO], 3–3.1 [1H, q, C$_6$H$_5$CH$\underline{H}$], 3.2–3.4 [3H, m, C$_6$H$_5$C$\underline{H}$H, NC$\underline{H}_2$CH$_2$CHC)], 3.8 [2H, d, NHC$\underline{H}_2$CO], 4.3–4.4 [1H, m, NHC$\underline{H}$CO], 4.5 [1H, m, NHC $\underline{H}$CO], 4.6–4.8 [1H, m, C$_6$H$_5$CH$_2$CH]. 5–5.2 [2H, m C$_6$H$_5$C $\underline{H}_2$OCO], 5.7 [1H, m, N$\underline{H}$], 6.8 [1H, d, N$\underline{H}$], 7–7.1 [1H, d, NH], 7.1–7.3 [5, m, C$_6$$\underline{H}_5$CH$_2$], 7.3–7.4 [5, m, C$_6$ $\underline{H}_5$CH$_2$OCO], 9.5 [1, s, C$\underline{H}$O].
4. Cbz-Pro-Gly-Ala-Leu-CHO:

δ0.8–1 [6H,m,CH(C$\underline{H}_3$)$_2$], 1.3–1.5 [3H,m,CH—C$\underline{H}_3$], 1.5–2.3 [7H,m,CHC$\underline{H}_2$C$\underline{H}$(CH$_3$)$_2$, C$\underline{H}_2$C$\underline{H}_2$CHNCHCO], 3.4–3.6 [2H,d,NHC$\underline{H}_2$CO],3.7–4.1 [2H,m,2×NHC$\underline{H}$CO], 4.1–4.3 [1H,m,NHC$\underline{H}$CO],4.3–4.6 [2H,m,NC$\underline{H}_2$CH$_2$CH$_2$CHCO], 5–5.2 [2H,m,C$_6$H$_5$C$\underline{H}_2$], 6.9–7.1 [1H, m,N$\underline{H}$],7.05–7.8 [8H,s,C$_6$$\underline{H}_5$3×N$\underline{H}$],9.5 [1H,d,C$\underline{H}$O].

5. Cbz-Gly-Pro-Ala-Phe-CHO:

δ1.2–1.4 [3H,m,C$\underline{H}_3$CH], 1.6–2.3 [4H,m,NCH$_2$C$\underline{H}_2$C$\underline{H}_2$CO], 3.0–3.8 [4H,m,C$_6$H$_5$C$\underline{H}_2$, NC$\underline{H}_2$CH$_2$CH$_2$CO], 3.83–4.1 [2H,m,NC$\underline{H}_2$CO],4.4–4.75 [3H,m,3×NC$\underline{H}$CO],5–5.25 [2H,m,C$_6$H$_5$C$\underline{H}_2$], 5.55–5.72 [H,m,N$\underline{H}$],6.95–7.5 [12H,m,2×C$_6$$\underline{H}_5$,2×N$\underline{H}$], 9.6 [1H,d,C$\underline{H}$O].

EXAMPLE 4

The proteolytic activities of the various components of the MPC were determined by utilizing synthetic peptide substrates specific for each component. Each of the substrates also contains a chromogenic moiety, the release of which upon cleavage by the MPC component provides a means for detecting cleavage.

The substrates Cbz-Gly-Gly-Leu-pNA, Cbz-D-Ala-Leu-Arg-2NA and Cbz-Leu-Leu-Glu-2NA were used to determine the activities of the ChT-L, T-L and PGPH components of the MPC, respectively, as previously described by Wilk and Orlowski, J. Neurochem. 35:1172–1182 (1980) and J. Neurochem 40:842–849 (1983), where pNA is p-nitroaniline and 2NA is 2-naphthylamide. The rate of release of the chromogenic group (aromatic amine) was measured after diazotization (Goldbarg & Rutenburg, Cancer 11:283–291 (1958) Bratton & Marshall, J. Biol. Chem. 128:537–550 (1939)).

Reaction mixtures contained 0.4 to 0.8 mM substrate, Tris-HCl buffer (0.05M; pH 8.0) and enzyme (1 to 3 µg) in a final volume of 0.25 ml. Incubations were at 37° C. The reactions were stopped by addition of an equal volume of 10% trichloroacetic acid and diazotization was then carried out.

Cbz-Gly-Pro-Ala-Leu-Gly-pAB and Cbz-Gly-Pro-Ala-Gly-Gly-pAB, where pAB is p-aminobenzoate, were used as convenient substrates for the determination of the activity of the BrAAP and SNAAP components respectively. The BrAAP component cleaves exclusively the Leu-Gly bond in Cbz-Gly-Pro-Ala-Leu-Gly-pAB, whereas the SNAAP component cleaves the Gly-Gly bond in Cbz-Gly-Pro-Ala-Gly-Gly-pAB.

A coupled two step reaction in the presence of excess aminopeptidase N (AN) was used for the determination of the BrAAP and SNAAP activities as described previously (Orlowski et al., Biochemistry 32:1563–1572 (1993)). Aminopeptidase N was purified from hog kidneys as described by Pfleiderer, Meth. Enzymol. 19:514–521 (1970) and freed from the contaminating metalloendopeptidase (EC 3.4.24.11) as previously described (Almenoff & Orlowski, Biochemistry 22:590–599 (1983)).

EXAMPLE 5

In vitro protein degrading activity of the MPC, and the effects of the various inhibitors of the present invention on such activity, was determined using β-casein and histone H$_3$ as proteolytic substrates. For determining protein degrading activity in the presence and absence of inhibitors, incubation mixtures contained Tris-HCl buffer (0.05M, pH 8.0), β-casein or histone H$_3$, 20 mM Mg$^{2+}$ where indicated, and inhibitor dissolved in dimethylsulfoxide, where indicated. In control samples, the inhibitor was replaced by an equal volume of dimethylsulfoxide alone.

In order to measure proteolysis by the MPC, and its inhibition by the inhibitors of the invention, aliquots of the reaction mixtures were removed after various incubation times and subjected to HPLC on a Deltapak column (C4; 5 µm; 300 A; 3.9×150 mm Waters). Elution of histone H$_3$ was carried out with a linear gradient over 30 min. established between 30 and 50% acetonitrile (v/v) in water containing 0.1% trifluoroacetic acid (v/v) at a flow rate of 1 ml/min. Elution of β-casein was carried with a linear gradient established between 10 and 45% acetonitrile (v/v) in water containing 0.1% trifluoroacetic acid (v/v). The rate of protein degradation was determined by measuring the decrease of the peak height of the protein compared with controls in which the enzyme was omitted. Alternatively degradation of the proteins was determined by integrating the area under the peak of the protein at time zero and determining the decrease of the area after incubation with the enzyme.

Histone H$_3$ used for testing the proteolytic activity of MPC was purified from a crude histone VIII S fraction (obtained from Sigma Chemical Co. St. Louis, Mo.) by HPLC. The material was applied to a Delta Pak C4-300A semipreparative column (15 µm; 7.8 mm×300 mm) equilibrated with 30% acetonitrile (v/v) in water solution, containing 0.1% trifluoroacetic acid (v/v). Elution was carried out at a flow rate of 4 ml/min with a linear, 50 min. gradient established between 30% and 50% acetonitrile (v/v) in water, each containing 0.1% trifluoroacetic acetic acid (v/v). The main protein peak was collected and the solvent was removed under reduced pressure. The protein was dissolved in water at a concentration of 1.85 mg/ml and used for experiments. The purified histone H$_3$ was subjected to HPLC on an analytical Deltapak column (C4; 5 µm; 300 A; 3.9×150 mm; Waters) with a linear gradient established between 30 and 50% acetonitrile (v/v) in water, containing 0.1% trifluoroacetic acid (v/v). A large protein peak with an average retention time of 25.5 min. was obtained. A small impurity eluting shortly before the main protein peak was also present. There was no attempt to eliminate this small peak. See, e.g., FIG. 2.

EXAMPLE 6

Inhibition constant ($K_i$) values for the inhibitors of the present invention towards the various proteolytic activities of the MPC were determined by the method of Dixon, Biochem. J. 55:170–171 (1953). Plots of 1/v vs [I] were made at three (3) different synthetic substrate concentrations and six (6) different inhibitor concentrations [I]. Linear regression analysis gave generally correlation coefficients better than 0.99.

Inhibition was tested with and without preincubation of the MPC with the inhibitors of the invention. No increase in inhibition was observed after preincubation of the enzyme with the inhibitor for up to 30 min, indicating absence of slow binding phenomena and a rapid equilibration between enzyme and inhibitor.

EXAMPLE 7

Table II provides a summary of the $K_i$ measurements for the various peptidyl aldehydes of the invention synthesized in accordance with Examples 2 and 3. BrAAP, SNAAP, ChT-L and PGPH activities were determined, using the substrates indicated in Table II.

Cbz-Gly-Pro-Phe-Leu-CHO (inhibitor 1 in Table I) was the strongest of the inhibitors of the BrAAP component, giving a $K_i$ of 1.5 µM. This inhibitor also inhibited the SNAAP component, albeit with a somewhat higher $K_i$. Due to the sigmoidal relationship between reaction rate and substrate concentration for the PGPH activity, only IC$_{50}$ values (inhibitor concentration giving 50% inhibition) at a substrate concentration of 0.64 mM were determined. An IC$_{50}$ value of 3.1 µM was obtained, showing the usefulness of the inhibitor for the inhibition of this component. Some inhibition of the ChT-L activity was also observed, although the K$_i$ for this component was almost 20 times higher than that for the other three activities. Neither Cbz-Gly-Pro-Phe-Leu-CHO, nor any of the other novel inhibitors of the invention listed in Table II had any inhibitory effect on the T-L activity of the MPC. Indeed, at the concentrations used, each of the inhibitors produced some activation of the T-L activity (data not shown).

Previous studies have shown that major portions of the PGPH and BrAAP activities of the MPC remain latent, and that full expression of these activities is only obtained in the presence of certain activators. Thus, depending on the substrate concentration, the PGPH activity could be increased almost 10-fold by addition to incubation mixtures of low concentrations of SDS (0.02%) or fatty acids such as lauric acid (Orlowski et al., Biochemistry 30:5999–6005 (1991)). Moreover, treatment of the MPC with SDS was shown to cause an almost 50-fold activation of the BrAAP component as measured with synthetic substrates. (Orlowski, et al., Biochemistry 32:1563–1572 (1993)). Furthermore, a 10-fold activation of the BrAAP component could also be obtained by treatment of the MPC with DCI (10 µM), an inhibitor concentration that causes almost complete inactivation of the PGPH activity (Cardozo et al. Biochemistry 31:7373–7380 (1992); Orlowski et al., Biochemistry 32:1563–1572 (1993)).

It was thus determined whether the inhibitors of the invention were active only toward the latent or toward both the overt and latent activities. The K$_i$ for Cbz-Gly-Pro-Phe-Leu-CHO was determined after full activation of the MPC with SDS (0.02%) and also after exposure of the MPC to DCI (10 µM). Identical IC$_{50}$ values (3.1 µM) were obtained for the PGPH activity in the presence and absence of SDS. Similarly, the BrAAP activity of the DCI-treated enzyme inhibited with a K$_i$ of 1.67 µM (average of three determinations), a value almost identical to that obtained for untreated native enzyme. Thus, Cbz-Gly-Pro-Phe-Leu-CHO is effective against both the overt and latent activities of the MPC.

Replacement of the phenylalanine residue in Cbz-Gly-Pro-Phe-Leu-CHO by an alanine residue (as in Cbz-Gly-Pro-Ala-Leu-CHO; inhibitor 3, Table II) increased the inhibition constant (K$_i$) for the BrAAP component by almost one order of magnitude, and similar decreases in inhibitory potency were seen for the other components of the complex. These results indicate the importance of a non-polar amino acid residue in the P$_2$ position for inhibitor binding. Other naturally-occurring amino acids e.g., Trp, and synthetic non-polar amino acids are believed to be equally effective in the P$_2$ position of the inhibitors of the invention.

Replacement of the Leu-CHO residue in Cbz-Gly-Pro-Phe-Leu-CHO by a Val-CHO residue (as in Cbz-Gly-Pro-Phe-Val-CHO; inhibitor 2, Table II) caused a thirty-fold increase in K$_i$ toward the BrAAP component, but a smaller decrease in inhibitory potency toward the SNAAP and ChT-L components. As a result, this inhibitor had a lower K$_i$ toward the SNAAP component than toward the BrAAP component.

Inhibitors 1–3 in Table II only weakly inhibited the ChT-L and PGPH activities, although Cbz-Gly-Pro-Phe-Leu-CHO appeared to be more inhibitory toward the latter component than either of the other two inhibitors. When Cbz-Gly-Pro-Phe-Leu-OH, the peptidyl alcohol precursor of Cbz-Gly-Pro-Phe-Leu-CHO was tested, no inhibition was observed at a concentration of up to 500 µM (data not shown).

The above indicated that the nature of residues in the P$_1$ and P$_2$ position is important for inhibitor potency i.e., a branched chain amino acid aldehyde, preferably Leu-CHO, but also Val-CHO in P$_1$ and a non-polar amino acid residue, e.g., Phe or Ala in P$_2$. The preference of the BrAAP component toward a branched chain amino acid residue in the P$_1$ position was also tested by replacing the P$_1$Leu-CHO residue in Cbz-Gly-Pro-Ala-Leu-CHO by a Phe-CHO to produce Cbz-Gly-Pro-Ala-Phe-CHO (inhibitor 5, Table II). This change dramatically affected the inhibition profile. Thus, the K$_i$ toward the BrAAP and SNAAP components increased by more than 20-fold indicating that an aromatic residue is not favored at the catalytic site of these components. Significantly, this change also caused a four-fold increase in the K$_i$ toward the ChT-L activity, with high K$_i$ (1850 mM) apparently being due to the presence of the Pro residue in the P$_3$ position.

The importance of the Pro residue in the P$_3$ for inhibition was also examined. Cbz-Pro-Gly-Ala-Leu-CHO (inhibitor 4, Table II), a peptidyl aldehyde in which the proline and glycine residues were transposed, shifting the proline residue from the P$_3$ position to the P$_4$ position and the glycine residue from the P$_4$ to the P$_3$ position, was tested for inhibitory activity. This change resulted in a marked loss in inhibitory potency against the BrAAP component, increasing the K$_i$ from 13.9 to 104 µM. Moreover, the transposition of the Pro and Gly residues caused an almost 30-fold decrease in K$_i$ for the ChT-L activity (from 471 to 16.4 µM) and only a two-fold increase of K$_i$ toward the SNAAP component. These changes show the importance of the Pro residue in the P$_3$ position for inhibition of the BrAAP component. It is also believed that proline analogs, such as hydroxyproline, would also be equally effective in the P$_3$ position. The presence of proline or a proline analog in P$_3$ does not favor interaction with the catalytic site of the ChT-L activity, since replacement of Pro by a Gly (e.g., inhibitor 4, Table II) changes the specificity of the peptidyl aldehyde from an inhibitor of the BrAAP component to that of a ChT-L component.

TABLE II

| | Inhibition of components of the multicatalytic proteinase complex by substrate-related peptidyl aldehydes. | | | | | | | |
|---|---|---|---|---|---|---|---|---|
| Component | BRAAP | | SNAAP | | ChT-L | | PGPH | |
| Peptidyl aldehyde | [I] µM | K$_i$ | [I] µM | K$_i$ | [I] µM | K$_i$ | [I] µM | IC$_{50}$ |
| 1. Cbz-Gly-Pro-Phe-Leu-CHO | [2.5–12.5] | 1.5 ± 0.17 | [2.5–12.5] | 2.3 ± 0.24 | [5–25] | 40.5 ± 8.8 | [2.5–12.5] | 3.1 ± 0.55 |
| 2. Cbz-Gly-Pro-Phe-Val-CHO | [10–50] | 47.3 ± 4.9 | [10–50] | 24.0 ± 0.84 | [30–150] | 331 ± 22 | [20–100] | 62 |
| 3. Cbz-Gly-Pro-Ala-Leu-CHO | [25–125] | 13.9 ± 1.9 | [10–50] | 17.2 ± 3.4 | [60–300] | 471 ± 48 | [20–100] | 60 |

TABLE II-continued

Inhibition of components of the multicatalytic proteinase complex by substrate-related peptidyl aldehydes.

| Component | BRAAP | | SNAAP | | ChT-L | | PGPH | |
|---|---|---|---|---|---|---|---|---|
| Peptidyl aldehyde | [I] μM | $K_i$ | [I] μM | $K_i$ | [I] μM | $K_i$ | [I] μM | $IC_{50}$ |
| 4. Cbz-Pro-Gly-Ala-Leu-CHO | [30–150] | 104 ± 2.3 | [10–100] | 36.7 ± 3.6 | [10–50] | 16.4 ± 2.7 | [20–100] | nd* |
| 5. Cbz-Gly-Pro-Ala-Phe-CHO | [100–500] | 305 ± 77 | [100–500] | 406 ± 54 | [100–500] | 1850 ± 750 | [200] | ni** |

Cbz-Gly-Pro-Ala-Leu-Gly-pAB (1 to 4 mill), Cbz-Gly-Pro-Ala-Gly-Gly-pAB (1 to 4 mill), Cbz-Gly-Gly-Leu-pNA (0.1 to 0.4 MM), and Cbz-Leu-Leu-Glu-2NA (0.2 to 0.6 mill) were used as substrates for the determination of activities of the branched amino acid preferring (BRAAP), small neutral amino acid preferring (SNAAP), chymotrypsin-like (ChT-L), and peptidylglutamyl-peptide hydrolyzing (PGPH) components respectively. Data are mean values from 3 to 6 experiments ± Standard error of the mean. For the PGPH activity, inhibitor concentrations giving 50% inhibition were measured.
*nd - not determined
**ni - no inhibition observed

EXAMPLE 8

The flexibility of the amino acid residue in the $P_4$ position of the inhibitors of the present invention is based on results of substrate specificity studies of the BrAAP component. Activities towards various analogs of the prototypic BrAAP substrate Cbz-Gly-Pro-Ala-Leu-Gly-pAB were determined using the coupled two-step reaction carried out in the presence of AN, as described in Example 4. The BrAAP substrates tested included the following:

Cbz-Gly-Pro-Ala-Leu-Gly-pAB; Cbz-Gly-Pro-Ala-Leu-Ala-pAB; Cbz-Leu-Gly-Ala-Leu-Ala-pAB; Cbz-Pro-Gly-Ala-Leu-Ala-pAB; and Cbz-Gly-Gly-Ala-Leu-Ala-pAB.

The kinetic parameters of degradation of the various substrates by the BrAAP component are summarized in Table III.

TABLE III

Kinetic parameters for degradation of synthetic substrates by the BRAAP component.

| Substrate | [S] (mM) | $K_m$ (mM) | $k_{cat}$ $(s^{-1})$ | $k_{cat}/K_m$ $(s^{-1}M^{-1})$ |
|---|---|---|---|---|
| 1. Cbz-Gly-Pro-Ala-Leu-Gly-pAB* | 1.6–8.0 | 5.2 | 3.75 | 720 |
| 2. Cbz-Gly-Pro-Ala-Leu-Ala-pAB* | 1.6–8.0 | 6.7 | 5.2 | 780 |
| 3. Cbz-Leu-Gly-Ala-Leu-Ala-pAB | 1.6–8.0 | 30 | 24 | 820 |
| 4. Cbz-Pro-Gly-Ala-Leu-Ala-pAB | 1.6–8.0 | 8.7 | 8.4 | 960 |
| 5. Cbz-Gly-Gly-Ala-Leu-Ala-pAB | 0.8–4.8 | 2.5 | 58 | 23,300 |

Data represent mean values for 2 separate determinations. For substrates with Michaelis-Menten kinetics, $K_m$ and $k_{cat}$ were determined from the regression line fitted to plots of 1/v vs 1/s. $K_{cat}$ was estimated assuming a molecular mabs of 700 KDa and assuming one active site per molecule. Substrate 5 displayed sigmoidal kinetics. The apparent Km for this substrate is taken as the substrate concentration at half of the $V_{max}$ observed. $k_{cat}$ for this substrate was calculated assuming a Vmax of 300 U/mg and assuming one active site per molecule of MPC.
*Data from Orlowski et al., Biochemistry 32:1563–1572 (1993).

EXAMPLE 9

The effect of the inhibitors of the invention on the protein degrading activity of the MPC was determined according to the protocol in Example 5. β-casein and histone $H_3$ were used as the substrates and Cbz-Gly-Pro-Ala-Leu-CHO was tested as the MPC inhibitor.

Figure 1:
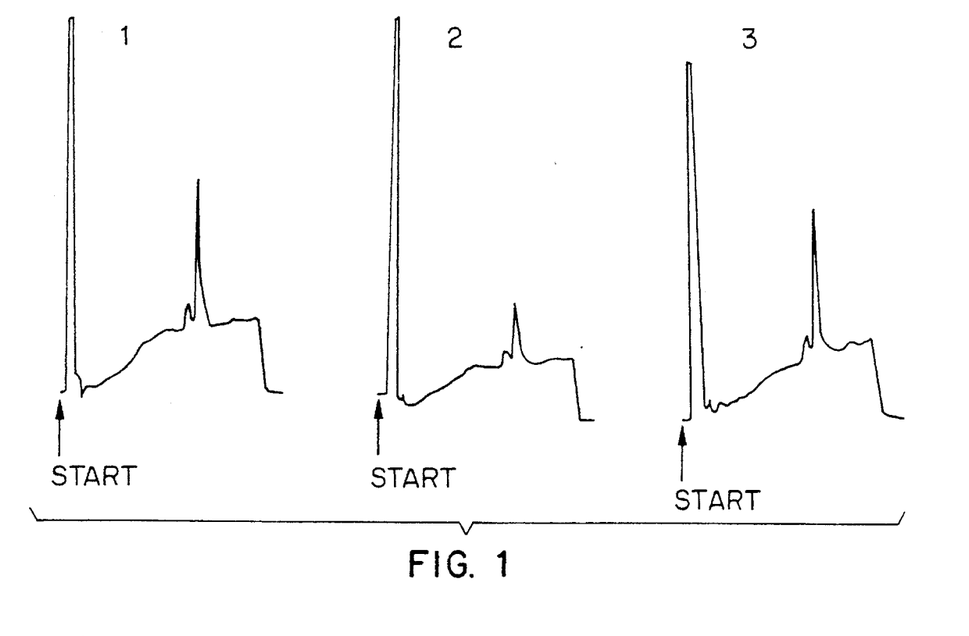
FIG. 1 is a high pressure liquid chromatograph chart showing inhibition of β-casein degradation by the MPC by Cbz-Gly-Pro-Ala-Leu-CHO.

FIG. 1 depicts the inhibition of β-casein degradation by Cbz-Gly-Pro-Ala-Leu-CHO. HPLC analyses were carried out on samples that had been incubated in the absence and presence of the inhibitor. Incubation mixtures contained β-casein (200 μg), 20 mM $Mg^{2+}$, MPC (30 μg) and various concentrations of, inhibitor, if used, in 2 μl of $Me_2SO$. Aliquots of the incubation mixture were subjected to HPLC as described in Example 5. Panel 1: Control reaction mixture at zero time. Panel 2: Reaction mixture after 30 min incubation with the enzyme in the absence of inhibitor. Panel 3: Reaction mixture after 30 min incubation in the presence of inhibitor (200 μM).

It may be clearly seen from FIG. 1 that β-casein was virtually completely degraded to a number of peptide fragments with shorter elution times (Panel 2). However, almost 90% of the β-casein substrate remained intact in the presence of 200 μM Cbz-Gly-Pro-Ala-Leu-CHO.

Figure 2:
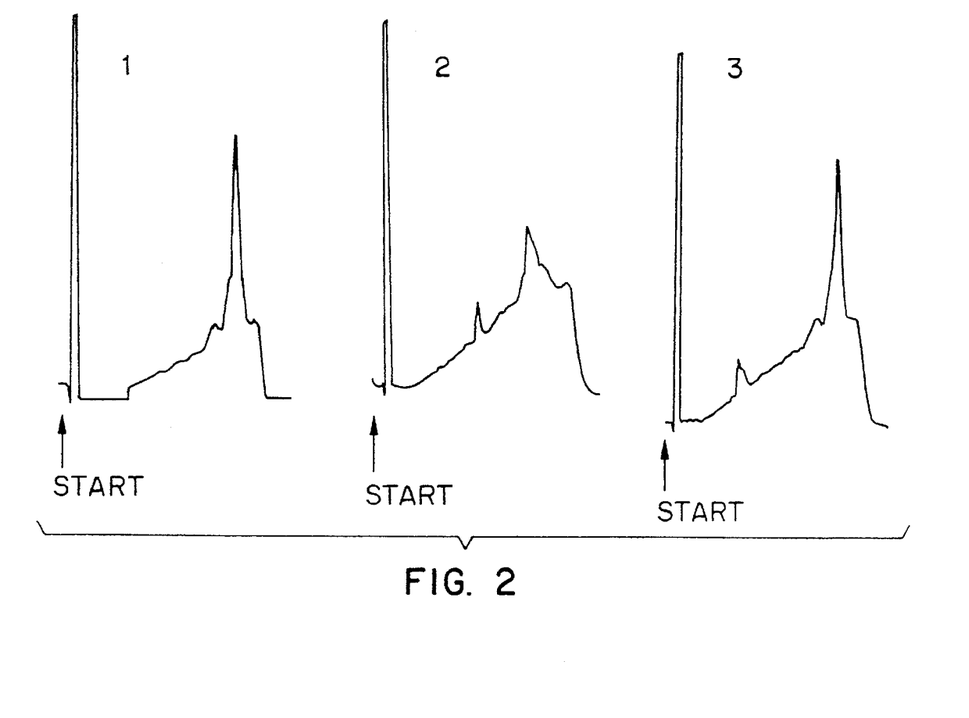
FIG. 2 is a high pressure liquid chromatograph showing inhibition of histone $H_3$ degradation by the MPC by Cbz-Gly-Pro-Ala-Leu-CHO.

FIG. 2 represents a similar inhibition experiment where histone $H_3$ was the substrate and Cbz-Gly-Pro-Ala-Leu-CHO was the MPC inhibitor. Incubation mixtures contained histone $H_3$ (55 μg), MPC (10 μg), inhibitor [(1.25 μl of a 20 mM solution in $Me_2SO$); final concentration 200 μM] and 0.05M Tris-HCl buffer (pH 8.0) in a final volume of 125 μl. In control samples the inhibitor was replaced by 1.25 μl of $Me_2SO$. Aliquots of the incubation mixture (25 μl) were subjected to HPLC as described in Example 5. Panel 1: Control reaction mixture at zero time. Panel 2: Reaction mixture after 15 min incubation with the enzyme in the absence of inhibitor. Panel 3. Reaction mixture after 15 min incubation with the enzyme in the presence of inhibitor (200 μM). As shown in FIG. 2, panel 3, the inhibitor at a concentration of 200 μM almost completely prevented degradation of histone $H_3$.

EXAMPLE 10

The inhibiting effects of Cbz-Gly-Pro-Phe-Leu-CHO on the degradation of histone $H_3$ and β-casein by the MPC are shown in Table IV. The rate of histone $H_3$ degradation by the MPC increased from 4.39 mg/mg MPC/hour to 14.98 mg/mg MPC/hour with the increase in histone concentration from 185 to 740 µg/ml of the incubation mixture. Additional increases in histone concentration to 1480 µg/ml did not further increase the rate of degradation (data not shown).

In the presence of 50 µM Cbz-Gly-Pro-Phe-Leu-CHO, the rate of degradation was inhibited by about 80% at all histone $H_3$ concentrations.

β-Casein was degraded by the MPC at a rate of 11.3 mg/mg MPC/h at a β-casein concentration of 0.16 mg/ml. Increasing the β-casein concentration to 1 mg/ml and addition of $Mg^{2+}$ increased the rate of degradation to 27.4 mg/mg MPC/h. At both concentrations the presence of 50 µM inhibitor resulted in inhibition of β-casein degradation by the MPC.

cells per wells in the presence and absence of Cbz-Gly-Pro-Phe-Leu-CHO or its peptidyl alcohol precursor. The results indicated that the inhibitor significantly inhibited cell proliferation of rat aortic smooth muscle cells at concentrations of 100–200 µM, while the corresponding alcohol precursor had minimal effects at the same concentrations.

In other experiments, similarly conducted, the inhibitor slowed proliferation of A 549 cells, a human lung carcinoma cell line (data not shown).

Flow cytometric analyses were conducted to determine at what stage in the cell cycle the inhibitor had its effect. Synchronized rat aortic smooth muscle cells were incubated for various periods of time in the presence and absence of Cbz-Gly-Pro-Phe-Leu-CHO, detached from culture plates and subjected to flow cytometry to determine cell cycle stage. The flow cytometric analyses (data not shown) indi-

TABLE IV

Effect of Cbz-Gly-Pro-Phe-Leu-CHO on the degradation of histone $H_3$ and βcasein by the multicatalytic proteinase complex (MPC).

| Protein | Concentration (µg/ml) | Incubation mixture: (µL) | $Mg^{2+}$ (mM) | MPC (µg) | Cbz-GPFL-CHO (µM) | Activity (µg/h/mgMPC) | Inhibition (percent) |
|---|---|---|---|---|---|---|---|
| Histone $H_3$ | 185 | 62.5 | — | 2.5 | — | 4,390 | — |
| " | 370 | 62.5 | — | 2.5 | — | 9,990 | — |
| " | 740 | 62.5 | — | 2.5 | — | 14,980 | — |
| " | 185 | 62.5 | — | 2.5 | 50 | 1,000 | 77 |
| " | 370 | 62.5 | — | 2.5 | 50 | 2,370 | 76 |
| " | 740 | 62.5 | — | 2.5 | 50 | 2,020 | 86 |
| β-casein | 160 | 125 | — | 5.0 | — | 11,330 | — |
| " | 160 | 125 | — | 5.0 | 50 | 670 | 94 |
| " | 1000 | 200 | 20 | 5.0 | — | 27,410 | — |
| " | 1000 | 200 | 20 | 5.0 | 50 | 2,960 | 89 |

Protein degradation as determined by HPLC as described in Example 5. Activity is expressed in µg of protein degraded per hour per mg of the MPC. Incubations were at 37° C. in Tris-HCl buffer, pH 8.0.

EXAMPLE 11

Previous reports in the literature, e.g., Glotzer et al., Nature (London) 349:132–138 (1991), have indicated that proteolysis plays a critical role in mitosis of the eukaryotic cell cycle. With this in mind, the effects of Cbz-Gly-Pro-Phe-Leu-CHO on the incorporation of $^3$H-thymidine and proliferation of cultured rat aortic smooth muscle cells, that had been derived from primary culture of dispersed rat aortic tissue, were examined. The cells, grown in wells of culture plates, were growth arrested at subconfluence (50–80% confluent) by serum deprivation. Cells were then stimulated to divide and proliferate by addition of serum back to the culture medium. Cell proliferation was monitored by measuring $^3$H-thymidine incorporation into individual cultures and by determining the number of cells per well, in the presence and absence of added Cbz-Gly-Pro-Phe-Leu-CHO.

Figure 3:
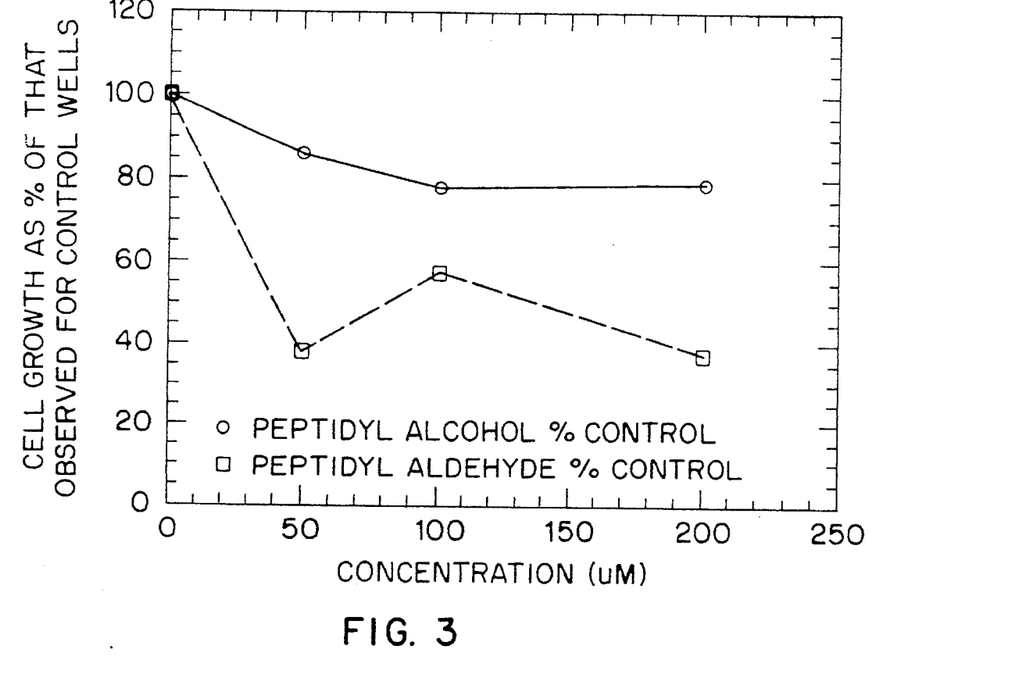
FIG. 3 is a chart showing inhibition of ³H-thymidine incorporation in dividing rat aortic smooth muscle cells by Cbz-Gly-Pro-Phe-Leu-CHO.

As shown in FIG. 3, the addition of various concentrations of Cbz-Gly-Pro-Phe-Leu-CHO to cultures significantly reduced $^3$H-thymidine incorporation, relative to wells that were not treated with inhibitor. FIG. 3 also shows the effects on cell division of cell cultures treated with equal concentrations of the inactive alcohol precursor (Example 2) of Cbz-Gly-Pro-Phe-Leu-CHO. The alcohol had little effect on $^3$H incorporation. Toxicity studies indicated that the inhibitor and its alcohol precursor were both non-toxic to cells at concentrations up to 200 µM, based on vital staining of cells with trypan-blue dye after 48–72 hours incubation with the agents.

Figure 4:
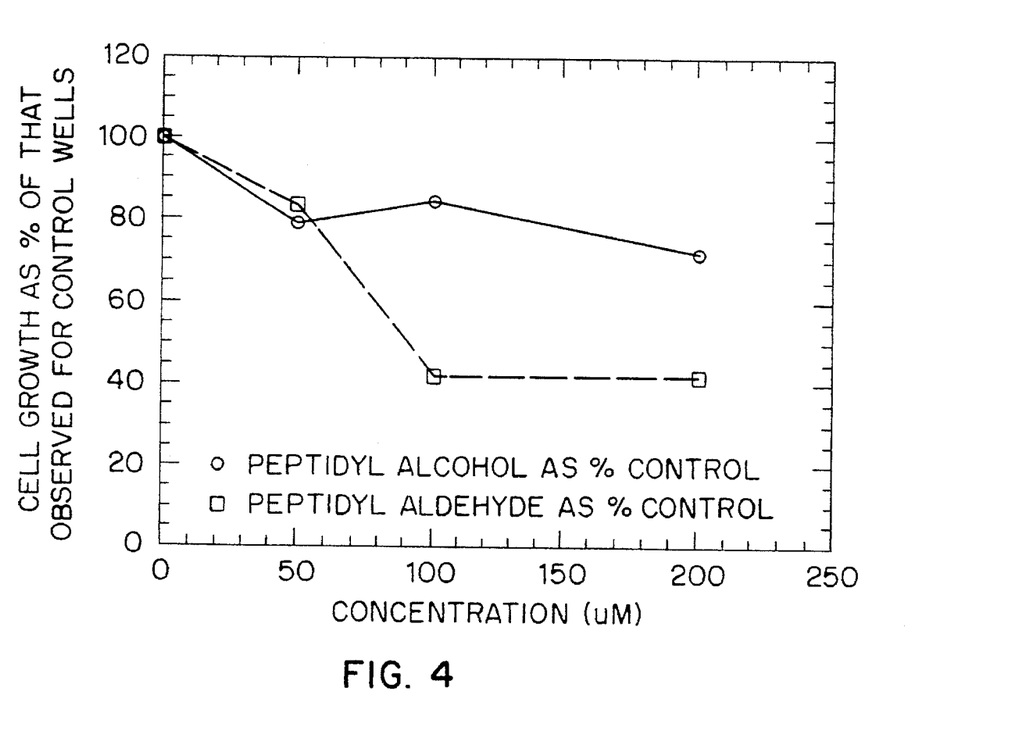
FIG. 4 is a chart showing a decrease in proliferation of dividing rat aortic smooth muscle cells in response to treatment by Cbz-Gly-Pro-Phe-Leu-CHO.

FIG. 4 shows that similar results were obtained when cell proliferation was evaluated by enumerating the number of cated an increase in the proportion of cells in the $G_2$/M phases in inhibitor treated versus untreated cultures. The data thus indicated that Cbz-Gly-Pro-Phe-Leu-CHO inhibits proliferation of cells in culture and that these effects are most likely a result in blockage of the procession of cells through the $G_2$/M phases.

EXAMPLE 12

The effects of the inhibitor Cbz-Gly-Pro-Phe-Leu-CHO on cell proliferation shown in Example 11 are believed to be caused by inhibition of the metabolism of key regulatory proteins, e.g., cyclins, involved in control of the mitotic cycle. Experiments were conducted to determine the effects of Cbz-Gly-Pro-Phe-Leu-CHO on intracellular protein degradation in A549 cells, the human lung carcinoma cell line of Example 11.

In order to measure intracellular protein degradation, cells were grown to confluence in culture wells in the absence of inhibitor. The confluent cell cultures were then pulsed with media containing $^{35}$S-methionine and then chased with cold media containing various concentrations of inhibitor or precursor alcohol, each dissolved in ethanol, for 30 minutes. Ethanol (equal volume) without inhibitor was added to control cultures. The added ethanol was not toxic to the cells. Protein degradation was quantitated by determining the percentage of the incorporated $^{35}$S-methionine that was released as trichioroactetic acid-soluble products (i.e., degraded proteins). This assay procedure primarily detects degradation of short-lived proteins, which are believed to be the target of the enzymatic activity of the MPC.

Figure 5:
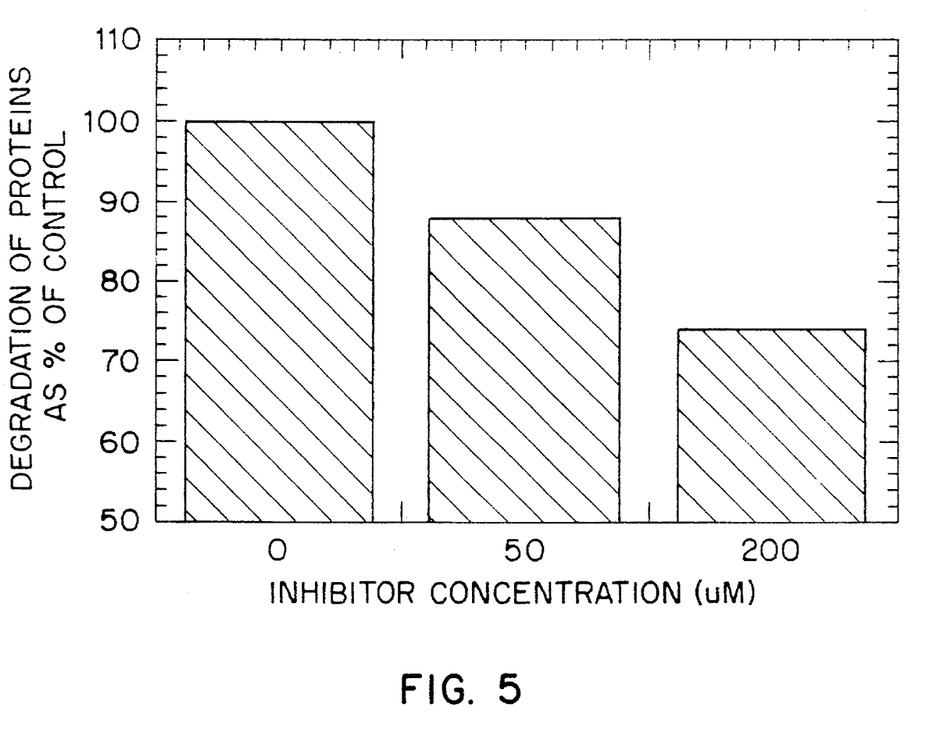
FIG. 5 is a chart showing a decrease in intracellular protein degradation in A549 cells mediated by treatment of the cells with Cbz-Gly-Pro-Phe-Leu-CHO.

As shown in FIG. 5, Cbz-Gly-Pro-Phe-Leu-CHO, at a concentration of 200 μM, significantly reduced degradation of short-lived proteins. In contrast, the alcohol precursor of the inhibitor, Cbz-Gly-Pro-Phe-Leu-OH, at concentrations up to 200 μM) did not inhibit intracellular protein degradation (data not shown). The results suggest that the effects of BrAAP component inhibitors of the invention on cell cycle progression is attributable to inhibition of intracellular proteolysis, which most likely is a result of the inhibition of the MPC.

We claim:

1. A peptidyl aldehyde having the general formula $$Z\text{-}P_4\text{-}P_3\text{-}P_2\text{-}P_1\text{-}CHO \qquad (I)$$

in which $P_1$ is selected from among leucine, valine and isoleucine;

$P_2$ is phenylalanine or alanine;

$P_3$ is proline or hydroxyproline;

$P_4$ is glycine;

CHO is an aldehyde replacement for the COOH group on the $P_1$ amino acid; and

Z is selected from among the group consisting of benzyloxycarbonyl, benzoylglycine, tertiary butoxycarbonyl and acetyl, wherein said peptidyl aldehyde is an inhibitor of the BrAAP component of the multicatalytic proteinase complex.

2. The peptidyl aldehyde according to claim 1 wherein Z is benzyloxycarbonyl.

3. The peptidyl aldehyde according to claim 1 wherein $P_1$ is leucine or valine.

4. The peptidyl aldehyde according to claim 1 wherein $P_1$ is leucine.

5. The peptidyl aldehyde according to claim 1 wherein $P_3$ is proline.

6. A peptidyl aldehyde having the amino acid sequence of SEQ ID NO. 1, in which a benzyloxycarbonyl group is attached to the $NH_2$ group of the N-terminal amino acid and the COOH group of the C-terminal amino acid is replaced by an aldehyde group, wherein said peptidyl aldehyde is an inhibitor of the BrAAP component of the multicatalytic proteinase complex (MPC) of cells.

7. A peptidyl aldehyde having the amino acid sequence of SEQ ID NO. 2, in which a benzyloxycarbonyl group is attached to the $NH_2$ group of the N-terminal amino acid and the COOH group of the C-terminal amino acid is replaced by an aldehyde group, wherein said peptidyl aldehyde is an inhibitor of the BrAAP component of the multicatalytic proteinase complex (MPC) of cells.

8. A peptidyl aldehyde having the amino acid sequence of SEQ ID NO. 3, in which a benzyloxycarbonyl group is attached to the $NH_2$ group of the N-terminal amino acid and the COOH group of the C-terminal amino acid is replaced by an aldehyde group, wherein said peptidyl aldehyde is an inhibitor of the BrAAP component of the multicatalytic proteinase complex (MPC) of cells.

9. A method of inhibiting proteolysis in cells catalyzed by the BrAAP component of the multicatalytic proteinase complex (MPC) comprising administering to cells a peptidyl aldehyde having the formula $$Z\text{-}P_4\text{-}P_3\text{-}P_2\text{-}P_1\text{-}CHO$$

in which $P_1$ is selected from among leucine, valine and isoleucine;

$P_2$ is phenylalanine or alanine;

$P_3$ is proline or hydroxyproline;

$P_4$ is glycine;

CHO is an aldehyde replacement for the COOH group on the $P_1$ amino acid; and

Z is selected from among the group consisting of benzyloxycarbonyl, benzoylglycine, tertiary butoxycarbonyl and acetyl, wherein said peptidyl aldehyde is an inhibitor of the BrAAP component of the multicatalytic proteinase complex (MPC) of cells and is administered to cells in an amount and for a time sufficient to inhibit cellular proteolysis catalyzed by the BrAAP component of the multicatalytic proteinase complex (MPC).

10. The method of inhibiting proteolysis according to claim 9 wherein Z is benzyloxycarbonyl.

11. The method of inhibiting proteolysis according to claim 9 wherein $P_1$ is leucine or valine.

12. The method of inhibiting proteolysis according to claim 9 wherein $P_1$ is leucine.

13. The method of inhibiting proteolysis according to claim 9 wherein $P_3$ is proline.

14. A method of inhibiting proteolysis in cells catalyzed by the BrAAP component of the multicatalytic proteinase complex (MPC) comprising administering to cells a peptidyl aldehyde having the amino acid sequence of SEQ ID NO. 1, in which a benzyloxycarbonyl group is attached to the $NH_2$ group of the N-terminal amino acid and the COOH group of the C-terminal amino acid is replaced by an aldehyde group, wherein said peptidyl aldehyde is an inhibitor of the BrAAP component of the multicatalytic proteinase complex (MPC) of cells in an amount and for a time sufficient to inhibit cellular proteolysis catalyzed by the BrAAP component of the multicatalytic proteinase complex (MPC).

15. A method of inhibiting proteolysis in cells catalyzed by the BrAAP component of the multicatalytic proteinase complex (MPC) comprising administering to cells a peptidyl aldehyde having the amino acid sequence of SEQ ID NO. 2, in which a benzyloxycarbonyl group is attached to the $NH_2$ group of the N-terminal amino acid and the COOH group of the C-terminal amino acid is replaced by an aldehyde group, wherein said peptidyl aldehyde is an inhibitor of the BrAAP component of the multicatalytic proteinase complex (MPC) of cells in an amount and for a time sufficient to inhibit cellular proteolysis catalyzed by the BrAAP component of the multicatalytic proteinase complex (MPC).

16. A method of inhibiting proteolysis in cells catalyzed by the BrAAP component of the multicatalytic proteinase complex (MPC) comprising administering to cells a peptidyl aldehyde having the amino acid sequence of SEQ ID NO. 3, in which a benzyloxycarbonyl group is attached to the $NH_2$ group of the N-terminal amino acid and the COOH group of the C-terminal amino acid is replaced by an aldehyde group, wherein said peptidyl aldehyde is an inhibitor of the BrAAP component of the multicatalytic proteinase complex (MPC) of cells, in an amount and for a time sufficient to inhibit cellular proteolysis catalyzed by the BrAAP component of the multicatalytic proteinase complex (MPC).

17. A method of inhibiting mitosis in proliferating cells comprising administering to said proliferating cells a peptidyl aldehyde having the formula $$Z-P_4-P_3-P_2-P_1-CHO$$

in which $P_1$ is selected from among leucine, valine and isoleucine;

$P_2$ is phenylalanine or alanine;

$P_3$ is proline or hydroxyproline;

$P_4$ is glycine;

CHO is an aldehyde replacement for the COOH group on the $P_1$ amino acid; and

Z is selected from among the group consisting of benzyloxycarbonyl, benzoylglycine, tertiary butoxycarbonyl and acetyl, wherein said peptidyl aldehyde is an inhibitor of the BrAAP component of the multicatalytic proteinase complex (MPC) of cells and is administered to proliferating cells in an amount and for a time sufficient to inhibit mitosis.

18. The method of inhibiting mitosis according to claim 17 wherein Z is benzyloxycarbonyl.

19. The method of inhibiting mitosis according to claim 17 wherein $P_1$ is leucine or valine.

20. The method of inhibiting mitosis according to claim 17 wherein $P_1$ is leucine.

21. The method of inhibiting mitosis according to claim 17 wherein $P_3$ is proline.

22. A method of inhibiting mitosis in proliferating cells comprising administering to proliferating cells a peptide aldehyde having the amino acid sequence of SEQ ID NO. 1, in which a benzyloxycarbonyl group is attached to the $NH_2$ group of the N-terminal amino acid and the COOH group of the C-terminal amino acid is replaced by an aldehyde group, wherein said peptidyl aldehyde is an inhibitor of the BrAAP component of the multicatalytic proteinase complex (MPC) of cells, in an amount and for a time sufficient to inhibit mitosis.

23. A method of inhibiting mitosis in proliferating cells comprising administering to proliferating cells a peptide aldehyde having the amino acid sequence of SEQ ID NO. 2, in which a benzyloxycarbonyl group is attached to the $NH_2$ group of the N-terminal amino acid and the COOH group of the C-terminal amino acid is replaced by an aldehyde group, wherein said peptidyl aldehyde is an inhibitor of the BrAAP component of the multicatalytic proteinase complex (MPC) of cells, in an amount and for a time sufficient to inhibit mitosis.

24. A method of inhibiting mitosis in proliferating cells comprising administering to proliferating cells a peptide aldehyde having the amino acid sequence of SEQ ID NO. 3, in which a benzyloxycarbonyl group is attached to the $NH_2$ group of the N-terminal amino acid and the COOH group of the C-terminal amino acid is replaced by an aldehyde group, wherein said peptidyl aldehyde is an inhibitor of the BrAAP component of the multicatalytic proteinase complex (MPC) of cells, in an amount and for a time sufficient to inhibit mitosis.

* * * * *

UNITED STATES PATENT AND TRADEMARK OFFICE
CERTIFICATE OF CORRECTION

PATENT NO. : 5,580,854          Page 1 of 2

DATED : December 3, 1996

INVENTOR(S) : Orlowski et al.

It is certified that error appears in the above-indentified patent and that said Letters Patent is hereby corrected as shown below:

Title page, delete Item 63 in its entirety;

Title page, 1st col., 8th-from-bottom line, "Beyon" should read --Beynon--;

Col. 1, delete lines 9-13;

Col. 1, line 28, "use" should read --use in--;

Col. 1, line 38, "cachexians" should read --cachexias,--;

Col. 6, line 65, "1522" should read --1572--;

Col. 7, line 32, "Coo" should read --Co.--;

Col. 10, line 32, "Peptidyle" should read --Peptidyl--;

Col. 14, line 20, "The preference ..." should start a new paragraph;

Col. 15, line 9, "4 mill" (both instances) should read -4 mM--;

Col. 15, line 9, "0.4 MM" should read --0.4 mM--;

Col. 15, line 10, "0.6 mill" should read --0.6 mM--;

UNITED STATES PATENT AND TRADEMARK OFFICE
CERTIFICATE OF CORRECTION

PATENT NO. : 5,580,854

DATED : December 3, 1996

INVENTOR(S) : Orlowski et al.

It is certified that error appears in the above-indentified patent and that said Letters Patent is hereby corrected as shown below:

Col. 15, 5th-from-bottom line of footnote to TABLE III, "mabs" should read --mass--;

Col. 15, 4th-from-bottom line of footnote to TABLE III, "Km" should read --$K_m$--;

Col. 17, 2nd line of TABLE IV, "βcasein" should read --β-casein--;

Col. 17, first line of footnote to TABLE IV, "as" should read --was--;

Col. 24, line 16, "peptide" should read --peptidyl--;

Col. 24, line 26, "peptide" should read --peptidyl--;

Col. 24, line 37, "peptide" should read --peptidyl--.

Signed and Sealed this

First Day of April, 1997

*Attest:*

BRUCE LEHMAN

*Attesting Officer*  Commissioner of Patents and Trademarks

UNITED STATES PATENT AND TRADEMARK OFFICE
CERTIFICATE OF CORRECTION

PATENT NO. : 5,580,854  
APPLICATION NO. : 08/206789  
DATED : December 3, 1996  
INVENTOR(S) : Marian Orlowski, Christopher Cardozo and Alexander Vinitsky Page 1 of 1

It is certified that error appears in the above-identified patent and that said Letters Patent is hereby corrected as shown below:

IN THE SPECIFICATION:

Please replace the paragraph beginning at Col. 1, line 6 and ending at Col. 1, line 8 with the following paragraph:

-- This invention was made with government support under grant numbers DK25377, DA07135, and HL08254 awarded by the National Institutes of Health. The United States Government has certain rights in the invention. --

Signed and Sealed this

Thirteenth Day of October, 2009

David J. Kappos  
*Director of the United States Patent and Trademark Office*

UNITED STATES PATENT AND TRADEMARK OFFICE
CERTIFICATE OF CORRECTION

PATENT NO. : 5,580,854
APPLICATION NO. : 08/206789
DATED : December 3, 1996
INVENTOR(S) : Marian Orlowski, Christopher Cardozo and Alexander Vinitsky Page 1 of 1

It is certified that error appears in the above-identified patent and that said Letters Patent is hereby corrected as shown below:

On the Title Pg, Item (63) delete entire section

"~~Related U.S. Application Data~~
~~[63] Continuation of Ser. No. 253,185, Jun, 2, 1994, abandoned,~~
~~which is a continuation of Ser. No. 68,273, May 26, 1993,~~
~~abandoned, which is a continuation of Ser. No. 801,324,~~
~~Dec. 2, 1991, abandoned.~~"

Signed and Sealed this

Seventeenth Day of May, 2011

David J. Kappos
*Director of the United States Patent and Trademark Office*